(12) United States Patent
Zha

(10) Patent No.: US 11,143,897 B2
(45) Date of Patent: Oct. 12, 2021

(54) LIQUID CRYSTAL DISPLAY DEVICE

(71) Applicant: WUHAN CHINA STAR OPTOELECTRONICS TECHNOLOGY CO., LTD., Wuhan (CN)

(72) Inventor: Guowei Zha, Wuhan (CN)

(73) Assignee: WUHAN CHINA STAR OPTOELECTRONICS TECHNOLOGY CO., LTD, Wuhan (CN)

( * ) Notice: Subject to any disclaimer, the term of this patent is extended or adjusted under 35 U.S.C. 154(b) by 483 days.

(21) Appl. No.: 16/309,068

(22) PCT Filed: Sep. 19, 2018

(86) PCT No.: PCT/CN2018/106419
§ 371 (c)(1),
(2) Date: Dec. 11, 2018

(87) PCT Pub. No.: WO2020/042248
PCT Pub. Date: Mar. 5, 2020

(65) Prior Publication Data
US 2021/0223591 A1   Jul. 22, 2021

(30) Foreign Application Priority Data

Aug. 31, 2018 (CN) .......................... 201811014146.6

(51) Int. Cl.
*G02F 1/133* (2006.01)
*G02F 1/1333* (2006.01)
(Continued)

(52) U.S. Cl.
CPC .... *G02F 1/13338* (2013.01); *G02F 1/133302* (2021.01); *G02F 1/133345* (2013.01);
(Continued)

(58) Field of Classification Search
CPC ........... G02F 1/13338; G02F 1/133512; G02F 1/133528; G02F 1/133617; G02F 2202/36; G02F 2203/11; G06K 9/0004
(Continued)

(56) References Cited

U.S. PATENT DOCUMENTS

2018/0142149 A1* 5/2018 Youn ...................... C09K 11/70
2018/0188583 A1* 7/2018 Liu ................... G02F 1/136227

* cited by examiner

*Primary Examiner* — Nathanael R Briggs
*Assistant Examiner* — William D Peterson
(74) *Attorney, Agent, or Firm* — Kirton McConkie; Evan R. Witt

(57) ABSTRACT

A liquid crystal display device is provided. The liquid crystal display device comprises a liquid crystal cell and a backlight module, and the liquid crystal cell comprises a color filter, an array substrate, a liquid crystal layer, an upper polarizer, and a lower polarizer. The color filter comprises a glass substrate, a plurality of black matrixes, and a plurality of color blocks, and the color blocks are doped with infrared quantum dots, the array substrate comprises a plurality of infrared sensing layers, the infrared sensing layers are located within corresponding shielding areas of the array substrate on which the black matrixes project. The in-panel recognition can be implemented through integrating the infrared quantum dots in the color blocks of the liquid crystal display device and disposing the infrared sensing layers in the shielding areas of the array substrate.

10 Claims, 4 Drawing Sheets

(51) Int. Cl.
*G02F 1/1335* (2006.01)
*G02F 1/13357* (2006.01)
*G06K 9/00* (2006.01)

(52) U.S. Cl.
CPC .. *G02F 1/133357* (2021.01); *G02F 1/133512* (2013.01); *G02F 1/133519* (2021.01); *G02F 1/133528* (2013.01); *G02F 1/133617* (2013.01); *G02F 2202/104* (2013.01); *G02F 2202/36* (2013.01); *G02F 2203/11* (2013.01); *G06K 9/0004* (2013.01)

(58) Field of Classification Search
USPC .......................................................... 349/12
See application file for complete search history.

LIQUID CRYSTAL DISPLAY DEVICE

FIELD OF INVENTION

The present disclosure relates to a display device, and in particular to a liquid crystal display device.

BACKGROUND OF INVENTION

In modern society, the interaction between people and displays has become an important way for people to access and share information, wherein liquid crystal displays have become the mainstream current display due to good picture reproducibility. The liquid crystal displays have gradually met the human eye's visual requirements for display quality in terms such as resolution, frame rate, color gamut, color shift, contrast, viewing angles, crosstalk, and flicker. In recent years, the breakthrough direction of mobile terminal display technology is to pay attention to integration of interactive technology and improvement of visual aesthetics. One important direction is the high-screen ratio of full-screen display technology. The key breakthroughs are the compression of the borders of the display panel, the camera and detector profile cutting, in-panel recognition, etc. In-panel recognition includes biometric recognition and imaging in-panel recognition, wherein traditional techniques of biometric recognition are fingerprint recognition and iris recognition, and the common practices of the imaging in-panel recognition adopt face recognition with depth perception.

At present, the more acceptable way for fingerprint recognition is to use fingerprint recognition technology. Traditional fingerprint recognition uses a solution that is integrated with a home button. However, full screen technology requirements make fingerprint in-panel recognition popular. There are three main types of fingerprint technology solutions: capacitive fingerprint, ultrasonic fingerprint, and optical fingerprint, wherein the optical fingerprint is the closest to mass production because it can penetrate thicker cover glass. Touch surface of the OLED has become the mainstream research and development technology.

The application of optical fingerprinting to LCD technology has also become the focus of current research breakthroughs. One difficulty is that a photodetector needs to be set in the identification area inside the panel. The photodetector inevitably affects transmittance and grayscale brightness of the identification area. There has not been a major breakthrough in battery technology. The power consumption of mobile terminals is still an important consideration for current liquid crystal displays. The balance of inside the panel fingerprint in-panel recognition and power consumption need to be overcome. The above problems are also common problems in the identification technology inside other panels. How to integrate the functional accessories of traditional mobile terminals into the display area and minimize the impact of display performance, it is a problem that comprehensive screen technology needs to overcome.

SUMMARY OF INVENTION

An object of the present disclosure is to provide a liquid crystal display device, and the in-panel recognition can be implemented through integrating the infrared quantum dots in the color blocks of the liquid crystal display device and disposing the infrared sensing layers in the shielding areas of the array substrate.

The present disclosure provides a liquid crystal display device, the liquid crystal display device comprises a liquid crystal cell and a backlight module, wherein the liquid crystal cell is disposed on the backlight module, and the backlight module is configured to provide a light source. The liquid crystal cell comprises a color filter, an array substrate, a liquid crystal layer, an upper polarizer, and a lower polarizer, the color filter is opposed to the array substrate, the liquid crystal layer is disposed between the color filter and the array substrate, the upper polarizer is attached to the color filter, and the lower polarizer is attached to the array substrate; the color filter comprises a glass substrate, a plurality of black matrixes, and a plurality of color blocks, the black matrixes are disposed on the glass substrate, the color blocks are disposed on the glass substrate, and the color blocks and the black matrixes are alternately arranged with each other. The color blocks are doped with infrared quantum dots, the array substrate comprises a plurality of infrared sensing layers, the infrared sensing layers are located within corresponding shielding areas of the array substrate on which the black matrixes project, the infrared sensing layers are configured to transmit at least one signal to a sensor chip, the infrared sensing layers are arranged along and located at a first side edge of the shielding area, and the first side edge of the shielding area is adjacent to the corresponding color blocks.

In one embodiment of the present disclosure, the color filter comprises an overcoat layer, and the black matrixes and the color blocks are located between the glass substrate and the overcoat layer.

In one embodiment of the present disclosure, the upper polarizer is disposed on an upper surface of the glass substrate, and the array substrate is disposed on the lower polarizer.

In one embodiment of the present disclosure, the upper polarizer is disposed on a lower surface of the overcoat layer, and the array substrate is disposed on the lower polarizer.

In one embodiment of the present disclosure, the infrared quantum dots comprise II-VI group semiconductor material or III-V group semiconductor material.

In one embodiment of the present disclosure, the II-VI group semiconductor material comprises CdS, CdSe, CdTe, or ZnSe, and the III-V group semiconductor material comprises InP or InAs.

In one embodiment of the present disclosure, each of the color blocks is an organic color resist or a dye, and the color blocks are doped with a dispersion agent.

In one embodiment of the present disclosure, the dispersion agent is selected from one or more of an amide based polymer, a modified polyurethane polymer, a high molecular block copolymer containing a pigment-philic group, a modified polyurethane, a modified polyacrylate, and a silicone surfactant.

In one embodiment of the present disclosure, the array substrate further comprises a substrate, a first buffer layer, a second buffer layer, a polysilicon layer, a gate insulating layer, a gate, an interlayer insulating layer, a source, a drain, a planarization layer, a common electrode, a passivation layer, and a pixel electrode. The first buffer layer is disposed on the substrate, the second buffer layer is disposed on the first buffer layer, the polysilicon layer is disposed on the second buffer layer, the gate insulating layer is disposed on the polysilicon layer, the gate is disposed on the gate insulating layer, the interlayer insulating layer is disposed on the gate insulating layer and the gate, the source and the drain are disposed on the interlayer insulating layer, the planarization layer is disposed on the source, the drain, and the interlayer insulating layer, the common electrode is disposed on the planarization layer, the passivation layer is disposed on the common electrode, the pixel electrode is disposed on the passivation layer, and the infrared sensing layers are disposed in the interlayer insulating layer.

In one embodiment of the present disclosure, the infrared sensing layers are arranged and located at the same side of the corresponding shielding areas.

The present disclosure further provides a liquid crystal display device, the liquid crystal display device comprises a liquid crystal cell and a backlight module, wherein the liquid crystal cell is disposed on the backlight module, and the backlight module is configured to provide a light source. The liquid crystal cell comprises a color filter, an array substrate, a liquid crystal layer, an upper polarizer, and a lower polarizer, the color filter is opposed to the array substrate, the liquid crystal layer is disposed between the color filter and the array substrate, the upper polarizer is attached to the color filter, and the lower polarizer is attached to the array substrate; the color filter comprises a glass substrate, a plurality of black matrixes, and a plurality of color blocks, the black matrixes are disposed on the glass substrate, the color blocks are disposed on the glass substrate, and the color blocks and the black matrixes are alternately arranged with each other. The color blocks are doped with infrared quantum dots, the array substrate comprises a plurality of infrared sensing layers, the infrared sensing layers are located within corresponding shielding areas of the array substrate on which the black matrixes project, the s are configured to transmit at least one signal to a sensor chip.

In one embodiment of the present disclosure, the color filter comprises an overcoat layer, and the black matrixes and the color blocks are located between the glass substrate and the overcoat layer.

In one embodiment of the present disclosure, the upper polarizer is disposed on an upper surface of the glass substrate, and the array substrate is disposed on the lower polarizer.

In one embodiment of the present disclosure, the upper polarizer is disposed on a lower surface of the overcoat layer, and the array substrate is disposed on the lower polarizer.

In one embodiment of the present disclosure, the infrared quantum dots comprise II-VI group semiconductor material or III-V group semiconductor material.

In one embodiment of the present disclosure, the II-VI group semiconductor material comprises CdS, CdSe, CdTe, or ZnSe, and the III-V group semiconductor material comprises InP or InAs.

In one embodiment of the present disclosure, each of the color blocks is an organic color resist or a dye, and the color blocks are doped with a dispersion agent.

In one embodiment of the present disclosure, the dispersion agent is selected from one or more of an amide based polymer, a modified polyurethane polymer, a high molecular block copolymer containing a pigment-philic group, a modified polyurethane, a modified polyacrylate, and a silicone surfactant.

In one embodiment of the present disclosure, the array substrate further comprises a substrate, a first buffer layer, a second buffer layer, a polysilicon layer, a gate insulating layer, a gate, an interlayer insulating layer, a source, a drain, a planarization layer, a common electrode, a passivation layer, and a pixel electrode. The first buffer layer is disposed on the substrate, the second buffer layer is disposed on the first buffer layer, the polysilicon layer is disposed on the second buffer layer, the gate insulating layer is disposed on the polysilicon layer, the gate is disposed on the gate insulating layer, the interlayer insulating layer is disposed on the gate insulating layer and the gate, the source and the drain are disposed on the interlayer insulating layer, the planarization layer is disposed on the source, the drain, and the interlayer insulating layer, the common electrode is disposed on the planarization layer, the passivation layer is disposed on the common electrode, the pixel electrode is disposed on the passivation layer, and the infrared sensing layers are disposed in the interlayer insulating layer.

In one embodiment of the present disclosure, the infrared sensing layers are arranged and located at the same side of the corresponding shielding areas.

As described above, the infrared sensing layers transmit signals to sensing IC through the array substrate, and the infrared sensing layers are disposed in the shielding areas A of the array substrate on which the black matrixes are project. It solves the problem that the detector is disposed inside the panel to affect the aperture ratio of the liquid crystal display device. In addition, the infrared quantum dots of the color filter can reduce the propagation distance of the optical sensing light to improve the sensitivity.

DETAILED DESCRIPTION OF PREFERRED EMBODIMENTS

Structure and technical means adopted by the present disclosure to achieve the above and other objects can be best understood by referring to the following detailed description of the preferred embodiments and the accompanying drawings. Furthermore, directional terms described by the present disclosure, such as upper, lower, front, back, left, right, inner, outer, side, longitudinal/vertical, transverse/horizontal, etc., are only directions by referring to the accompanying drawings, and thus the used directional terms are used to describe and understand the present disclosure, but the present disclosure is not limited thereto.

Figure 1:
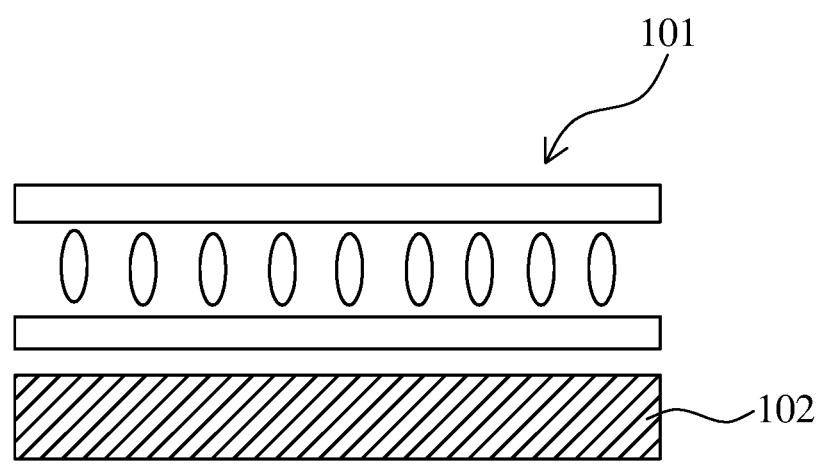
FIG. 1 is a schematic diagram of a liquid crystal display device according to a first preferred embodiment of the present disclosure.
Figure 2A:
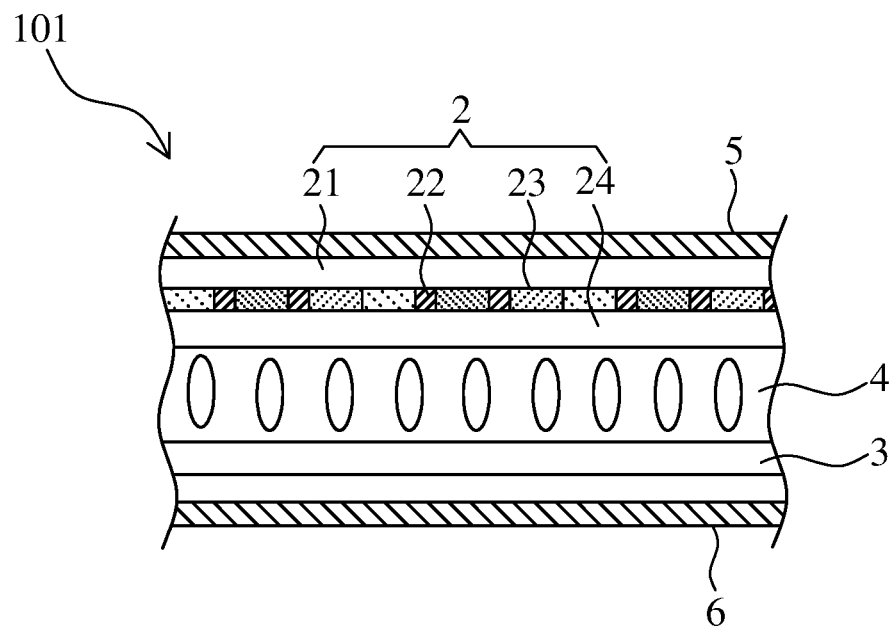
FIG. 2A is a schematic diagram of a liquid crystal cell of the liquid crystal display device according to the first preferred embodiment of the present disclosure.

Referring to FIGS. 1 and 2A, a schematic diagram of a liquid crystal display device and a schematic diagram of a liquid crystal cell of the liquid crystal display device according to a first preferred embodiment of the present disclosure are illustrated. The liquid crystal display device comprises a liquid crystal cell 101 and a backlight module 102, wherein the liquid crystal cell 101 is disposed on the backlight module 102, and the backlight module 102 is configured to provide a light source. The liquid crystal cell 101 comprises a color filter 2, an array substrate 3, a liquid crystal layer 4, an upper polarizer 5, and a lower polarizer 6. The detailed structure of each component, assembly relationships, and principles of operation for the present invention will be described in detail hereinafter.

Referring to FIGS. 1 and 2A, the color filter 2 is opposed to the array substrate 3, the liquid crystal layer 4 is disposed between the color filter 2 and the array substrate 3, the upper polarizer 5 is attached to the color filter 2, and the lower polarizer 6 is attached to the array substrate 3.

Referring to FIGS. 1 and 2A, the color filter 2 comprises a glass substrate 21, a plurality of black matrixes 22, a plurality of color blocks 23, and an overcoat layer 24, wherein the black matrixes 22 are disposed on the glass substrate 21, the color blocks 23 are disposed on the glass substrate 21, and the color blocks 23 and the black matrixes 22 are alternately arranged with each other. The black matrixes 22 and the color blocks 23 are located between the glass substrate 21 and the overcoat layer 24.

Referring to FIGS. 1 and 2A, in the embodiment, the overcoat layer 24 is attached to the liquid crystal layer 4, the black matrixes 22 and the color blocks 23 and are attached to the overcoat layer 24, and the glass substrate 21 is attached to the black matrixes 22 and the color blocks 23. The upper polarizer 5 is disposed on an upper surface of the glass substrate 21.

Referring to FIGS. 1 and 2A, the color blocks 23 are doped with infrared quantum dots, wherein the infrared quantum dots comprise II-VI group semiconductor material or III-V group semiconductor material. In the embodiment, the II-VI group semiconductor material comprises CdS, CdSe, CdTe, or ZnSe, and the III-V group semiconductor material comprises InP or InAs. In addition, each of the color blocks 23 is an organic color resist or a dye, and the color blocks 23 are doped with a dispersion agent, which can effectively disperse the infrared quantum dots to avoid agglomeration of the infrared quantum dots. In the embodiment, the dispersion agent is selected from one or more of an amide based polymer, a modified polyurethane polymer, a high molecular block copolymer containing a pigmentphilic group, a modified polyurethane, a modified polyacrylate, and a silicone surfactant.

Figure 3A:
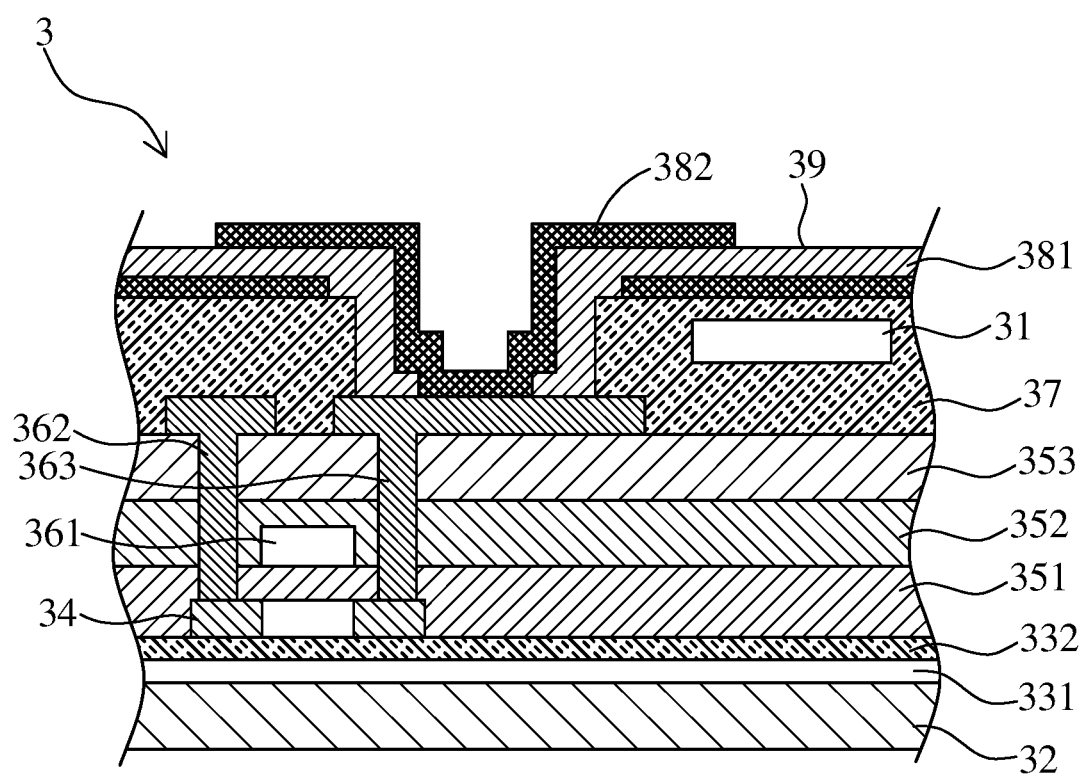
FIG. 3A is a schematic diagram of an array substrate of the liquid crystal display device according to the first preferred embodiment of the present disclosure.

Referring to FIGS. 2A and 3A, the array substrate 3 is disposed on the lower polarizer 6, and the array substrate 3 comprises a plurality of infrared sensing layers 31, a substrate 32, a first buffer layer 331, a second buffer layer 332, a polysilicon layer 34, a gate insulating layer 351, a gate 361, an interlayer insulating layer 352, a spacer layer 353, a source 362, a drain 363, a planarization layer 37, a common electrode 381, a passivation layer 39, and a pixel electrode 382.

Referring to FIG. 3A, the first buffer layer 331 is disposed on the substrate 32, the second buffer layer 332 is disposed on the first buffer layer 331, the polysilicon layer 34 is disposed on the second buffer layer 332, the gate insulating layer 351 is disposed on the polysilicon layer 34, the gate 361 is disposed on the gate insulating layer 351, the interlayer insulating layer 352 is disposed on the gate insulating layer 351 and the gate 361, the spacer layer 353 is disposed on the interlayer insulating layer 352, the source 362 and the drain 363 are disposed on the spacer layer 353, the planarization layer 37 is disposed on the source 362, the drain 363, and the spacer layer 353, the common electrode 381 is disposed on the planarization layer 37, the passivation layer 39 is disposed on the common electrode 381, the pixel electrode 382 is disposed on the passivation layer 39, and the infrared sensing layers 31 are disposed in the planarization layer 37.

Figure 3B:
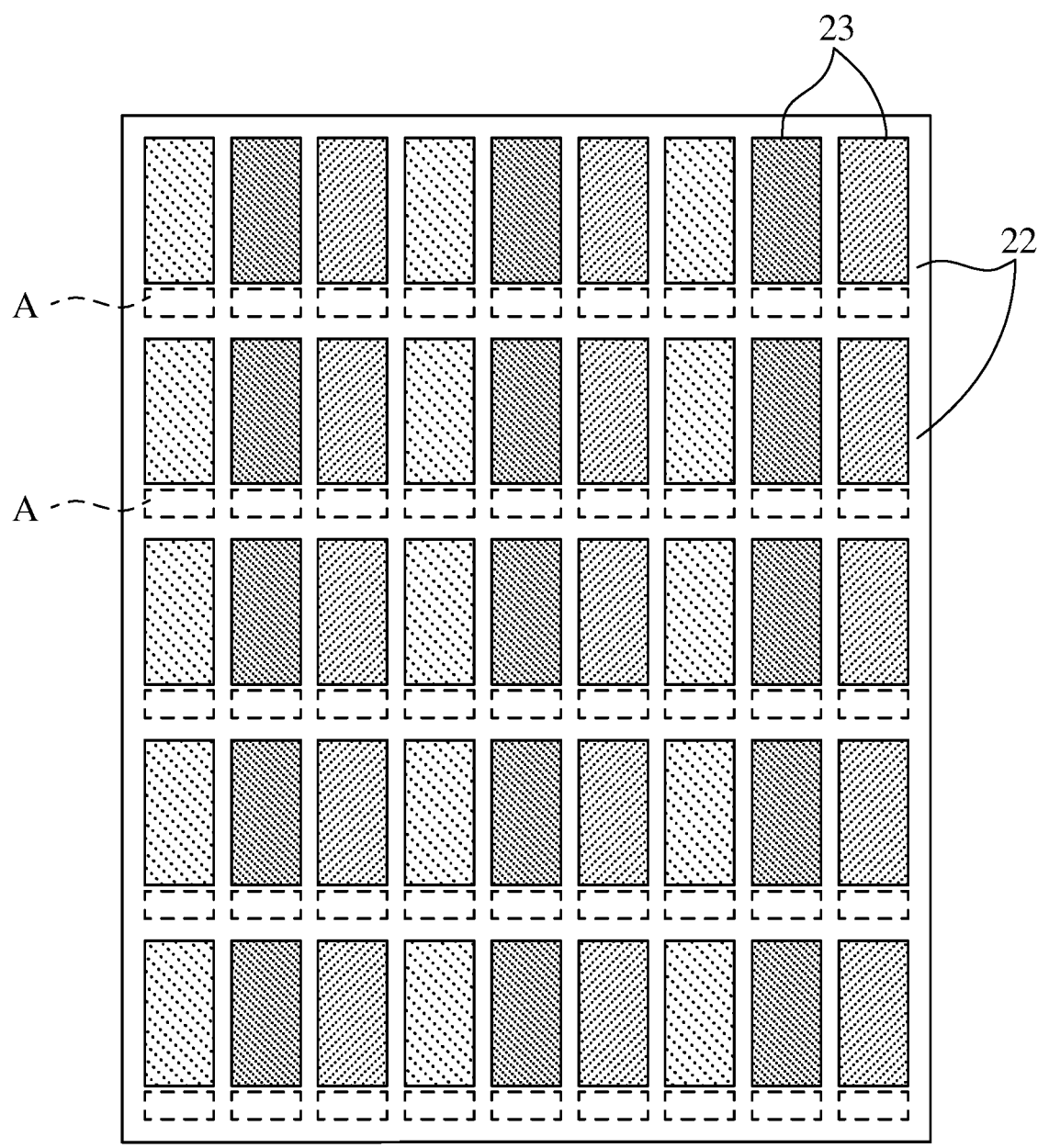
FIG. 3B is a schematic diagram of an array substrate of the liquid crystal display device according to the second preferred embodiment of the present disclosure.

Referring to FIGS. 3A and 3B, the infrared sensing layers 31 are located within corresponding shielding areas A of the array substrate 3 on which the black matrixes 22 project. The infrared sensing layers 31 are infrared sensors and configured to transmit at least one signal to a sensor chip (not shown). In the embodiment, the infrared sensing layers 31 are arranged and located at the same side of the corresponding shielding areas A. For example, the infrared sensing layers 31 are arranged and located at a first side edge of the corresponding shielding areas A, and the first side edge of the corresponding shielding areas A are adjacent to the corresponding color blocks 23.

According to the described structure, the color filter 2 excites red, green, and blue after the light of the backlight module 102 is irradiated, and the color filter 2 emit infrared rays at the same time. The wavelength of the infrared ray is associated with the diameter of the infrared quantum dot. When the diameter of the infrared quantum dot is larger, the wavelength of the infrared ray is larger. The wavelength of the infrared ray is close to the optimum response wavelength of the infrared sensing layers 31 of the array substrate 3, and able to effectively respond to the infrared sensing signal. In general, the array substrate 3 can be used for fingerprint recognition of a panel. The infrared quantum dots emit photons, light signals are reflected through the fingerprint, the information of fingerprint is obtained by the identification of the infrared sensing layers 31. In addition, the array substrate 3 is also suitable for biometric, human imaging, facial recognition, or iris recognition.

As described above, the in-panel recognition can be implemented through integrating the infrared quantum dots in the color blocks 23 of the liquid crystal display device and disposing the infrared sensing layers 31 in the shielding areas A of the array substrate 3. The infrared quantum dots are excited by blue, green, or red of the liquid crystal display device. The infrared sensing layers 31 transmit signals to sensing IC through the array substrate 3, and the infrared sensing layers 31 are disposed in the shielding areas A of the array substrate 3 on which the black matrixes 22 are project. It solves the problem that the detector is disposed inside the panel to affect the aperture ratio of the liquid crystal display device. In addition, the infrared quantum dots of the color filter 2 can reduce the propagation distance of the optical sensing light to improve the sensitivity. The emission of the infrared quantum dots is in units of pixels or sub-pixels. Therefore, the resolution of the in-panel recognition can be improved to achieve high-resolution 3D imaging capabilities inside the panel.

Figure 2B:
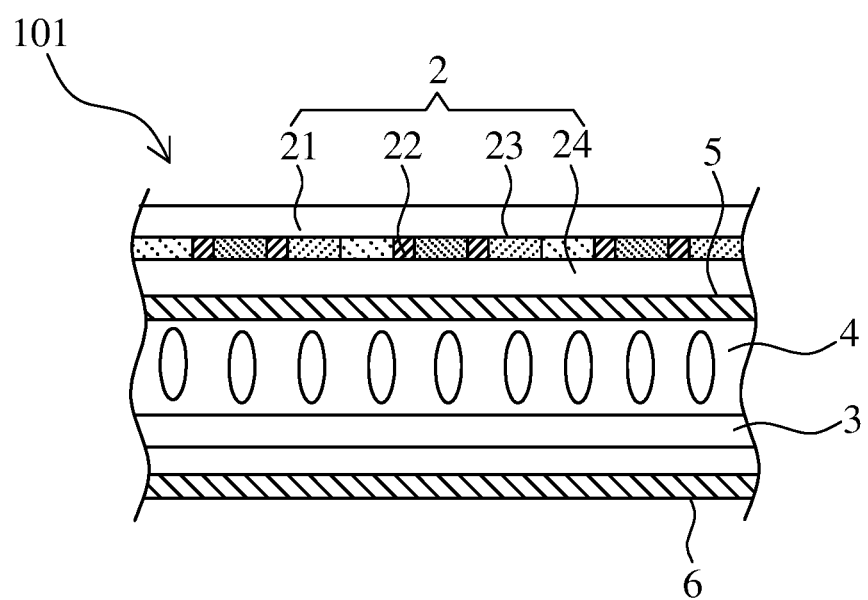
FIG. 2B is a schematic diagram of a liquid crystal cell of the liquid crystal display device according to a second preferred embodiment of the present disclosure.

Referring to FIGS. 1 and 2B, a schematic diagram of a liquid crystal display device and a schematic diagram of a liquid crystal cell of the liquid crystal display device according to a second preferred embodiment of the present disclosure are illustrated, wherein the second preferred embodiment is similar to the first preferred embodiment. The liquid crystal cell 101 comprises a color filter 2, an array substrate 3, a liquid crystal layer 4, an upper polarizer 5, and a lower polarizer 6, the difference of the second preferred embodiment is that the upper polarizer 5 is attached to the liquid crystal layer 4, and disposed on a lower surface of an overcoat layer 24 of the color filter 2. The overcoat layer 24 is attached to the upper polarizer 5, the black matrixes 22 and the color blocks 23 are attached to the overcoat layer 24, and a glass substrate 21 of the color filter 2 is attached to the black matrixes 22 and the color blocks 23.

As described above, the in-panel recognition can be implemented through integrating the infrared quantum dots in the color blocks 23 of the liquid crystal display device and disposing the infrared sensing layers 31 in the shielding areas A of the array substrate 3. The infrared quantum dots are excited by blue, green, or red of the liquid crystal display device. The infrared sensing layers 31 transmit signals to sensing IC through the array substrate 3, and the infrared sensing layers 31 are disposed in the shielding areas A of the array substrate 3 on which the black matrixes 22 are project. It solves the problem that the detector is disposed inside the panel to affect the aperture ratio of the liquid crystal display device. In addition, the infrared quantum dots of the color filter 2 can reduce the propagation distance of the optical sensing light to improve the sensitivity. The emission of the infrared quantum dots is in units of pixels or sub-pixels. Therefore, the resolution of the in-panel recognition can be improved to achieve high-resolution 3D imaging capabilities inside the panel.

The present disclosure has been described with preferred embodiments thereof and it is understood that many changes and modifications to the described embodiments can be carried out without departing from the scope and the spirit of the invention that is intended to be limited only by the appended claims.

What is claimed is:

1. A liquid crystal display device, comprising:
   a liquid crystal cell and a backlight module, wherein the liquid crystal cell is disposed on the backlight module, and the backlight module is configured to provide a light source;
   wherein the liquid crystal cell comprises a color filter, an array substrate, a liquid crystal layer, an upper polarizer, and a lower polarizer, the color filter is opposed to the array substrate, the liquid crystal layer is disposed between the color filter and the array substrate, the upper polarizer is attached to the color filter, and the lower polarizer is attached to the array substrate; the color filter comprises a glass substrate, a plurality of black matrixes, and a plurality of color blocks, the black matrixes are disposed on the glass substrate, the color blocks are disposed on the glass substrate, and the color blocks and the black matrixes are alternately arranged with each other; and
   wherein the color blocks are doped with infrared quantum dots, the array substrate comprises a plurality of infrared sensing layers, the infrared sensing layers are located within corresponding shielding areas of the array substrate on which the black matrixes project, the infrared sensing layers are configured to transmit at least one signal to a sensor chip, the infrared sensing layers are arranged along and located at a first side edge of the shielding area, and the first side edge of the shielding area is adjacent to the corresponding color blocks.

2. The liquid crystal display device according to claim 1, wherein the color filter comprises an overcoat layer, and the black matrixes and the color blocks are located between the glass substrate and the overcoat layer.

3. The liquid crystal display device according to claim 2, wherein the upper polarizer is disposed on an upper surface of the glass substrate, and the array substrate is disposed on the lower polarizer.

4. The liquid crystal display device according to claim 2, wherein the upper polarizer is disposed on a lower surface of the overcoat layer, and the array substrate is disposed on the lower polarizer.

5. The liquid crystal display device according to claim 1, wherein the infrared quantum dots comprise II-VI group semiconductor material or III-V group semiconductor material.

6. The liquid crystal display device according to claim 5, wherein the II-VI group semiconductor material comprises CdS, CdSe, CdTe, or ZnSe, and the III-V group semiconductor material comprises InP or InAs.

7. The liquid crystal display device according to claim 1, wherein each of the color blocks is an organic color resist or a dye, and the color blocks are doped with a dispersion agent.

8. The liquid crystal display device according to claim 7, wherein the dispersion agent is selected from one or more of an amide based polymer, a modified polyurethane polymer, a high molecular block copolymer containing a pigment-philic group, a modified polyurethane, a modified polyacrylate, and a silicone surfactant.

9. The liquid crystal display device according to claim 1, wherein the array substrate further comprises a substrate, a first buffer layer, a second buffer layer, a polysilicon layer, a gate insulating layer, a gate, an interlayer insulating layer, a source, a drain, a planarization layer, a common electrode, a passivation layer, and a pixel electrode;
   wherein the first buffer layer is disposed on the substrate, the second buffer layer is disposed on the first buffer layer, the polysilicon layer is disposed on the second buffer layer, the gate insulating layer is disposed on the polysilicon layer, the gate is disposed on the gate insulating layer, the interlayer insulating layer is disposed on the gate insulating layer and the gate, the source and the drain are disposed on the interlayer insulating layer, the planarization layer is disposed on the source, the drain, and the interlayer insulating layer, the common electrode is disposed on the planarization layer, the passivation layer is disposed on the common electrode, the pixel electrode is disposed on the passivation layer, and the infrared sensing layers are disposed in the interlayer insulating layer.

10. The liquid crystal display device according to claim 9, wherein the infrared sensing layers are arranged and located at the same side of the corresponding shielding areas.

\* \* \* \* \*